United States Patent [19]

Sheaff

[11] Patent Number: 5,211,631
[45] Date of Patent: May 18, 1993

[54] PATIENT WARMING APPARATUS

[76] Inventor: Charles M. Sheaff, 232 Hampton Ct., Palatine, Ill. 60067

[21] Appl. No.: 734,935

[22] Filed: Jul. 24, 1991

[51] Int. Cl.$^5$ .................. A61M 31/00; A61F 7/12; A61F 7/00; H05B 7/12
[52] U.S. Cl. .................. 604/113; 604/65; 604/96; 604/100; 604/264; 128/400; 128/401
[58] Field of Search .................. 604/52, 53, 43, 65, 604/82, 93, 96, 100, 102, 113, 263, 264, 286, 268, 291; 128/786, 692, 713, 399–401; 606/192; 165/142, 154

[56] References Cited

U.S. PATENT DOCUMENTS

| 550,238 | 11/1895 | Allen, Jr. |
| 2,910,981 | 11/1959 | Wilson et al. |
| 3,036,818 | 5/1962 | Legrand ............... 165/154 |
| 3,228,460 | 1/1966 | Garwin ............... 165/154 |
| 3,448,739 | 6/1969 | Stark et al. |
| 3,633,579 | 1/1972 | Alley ............... 604/53 |
| 3,634,924 | 1/1972 | Blake et al. |
| 3,726,269 | 4/1973 | Webster, Jr. |
| 3,746,003 | 7/1973 | Blake et al. |
| 3,833,004 | 9/1974 | Vazquez et al. |
| 3,924,628 | 12/1975 | Droegemueller et al. |
| 3,995,623 | 12/1976 | Blake et al. |
| 4,329,994 | 5/1982 | Cooper. |
| 4,372,374 | 2/1983 | Lee ............... 165/154 |
| 4,407,304 | 10/1983 | Lieber et al. |
| 4,632,125 | 12/1986 | Webler et al. |
| 4,651,751 | 3/1987 | Swendson et al. |
| 4,681,122 | 7/1987 | Winters et al. |
| 4,745,928 | 5/1988 | Webler et al. |
| 4,747,826 | 5/1988 | Sassano. |
| 4,754,752 | 7/1988 | Ginsburg et al. |
| 4,796,640 | 1/1989 | Webler. |
| 4,850,334 | 7/1989 | Cassagne et al. ............... 165/142 |
| 4,874,359 | 10/1989 | White et al. |
| 4,993,430 | 2/1991 | Shimoyama et al. |
| 5,084,044 | 1/1992 | Quint ............... 604/96 |

Primary Examiner—Randall L. Green
Assistant Examiner—P. Z. Harelli
Attorney, Agent, or Firm—Welsh & Katz

[57] ABSTRACT

Patient warming apparatus includes a catheter which mixes relatively hot intravenous fluids with the patient's blood without excessive tissue damage, by monitoring the temperature of the mixed blood and the core temperature of the patient. The fluids are heated to about 50°–100° C. The catheter is surrounded by a relatively large diameter introducer sheath, and is spaced from the sheath by a cooling jacket. Unheated fluid is passed through the cooling jacket to thermally isolate the heated infusate from the patient, to prevent entry site and endothelial burning. An external computer control system monitors and controls both the body core temperature of the patient and the temperature and flow rate of the infusate.

10 Claims, 4 Drawing Sheets

PATIENT WARMING APPARATUS

This invention relates to patient warming methods and apparatus, and more particularly, to catheters and control systems for infusing relatively high temperature fluids into a body, without excessive entry site or endothelial burning.

BACKGROUND OF THE INVENTION

A catheter is a slender, hollow tube which is inserted into a body passage, vessel or cavity. Among other things, catheters are used to infuse fluids into a patient through an artificial opening in the patient's body. For example, intravenous fluid is often infused by inserting a catheter through the skin at an entry site and into a blood vein, and injecting the fluid into the body by passing it through the catheter.

When a patient loses a significant amount of blood, or is exposed to surgery or anaesthesia for long times, body temperature may drop. In such situations, heated fluids may be infused in order to raise the body temperature. However, the maximum temperature of the heated fluid is ordinarily about 41° C., to avoid burns or other damage to the blood tissue or internal organs.

It has recently been discovered that relatively hot infusion fluids can significantly reduce the recovery time of patients who suffer from such temperature losses, provided that the temperature of the blood stream after mixing is not greater than 41° C. The temperature of the fluids can be about 50°–100° C.

There is a need for a catheter to provide rapid mixing of hot fluids with the bloodstream in a controlled fashion that prevents the mixed blood from exceeding 41° C. Such a catheter would also require thermal isolation from entry site tissues to prevent tissue burns.

Accordingly, one object of this invention is to provide new and improved patient warming methods and apparatus.

Another object is to provide new and improved control systems which accurately maintain desired temperatures and flow rates when relatively high temperature fluids are infused through an opening in a patient's body.

Still another object is to provide new and improved catheters for infusing relatively high temperature fluids into a patient's body, without excessive entry site or endothelial burning.

SUMMARY OF THE INVENTION

In keeping with one aspect of this invention, patient warming apparatus includes a relatively large diameter introducer sheath and a coaxial catheter inside the sheath. The catheter is centered in the sheath by a plurality of buttons, ribs or the like between the sheath and the catheter, or by narrowing the distal end of the sheath. The buttons or narrow sheath end create a space between the catheter and the sheath which becomes a cooling jacket when cool fluids are passed through the space.

In use, the sheath is inserted into a blood vein or the like through an artificial opening in a patient's body known as an entry site, using known insertion devices and techniques. After the sheath is in place, the catheter is placed inside the sheath. The catheter is longer than the sheath, and extends beyond the end of the sheath so that the end of the catheter is in a selected place in the patient's body. Crystalloid or another suitable fluid having a temperature of about 20°–30° C. is placed in the cooling jacket, and an infusate having a temperature of about 50°–100° C. is injected into the patient's body through the catheter. The coolant in the jacket thermally isolates the heated fluids from the tissue surrounding the opening, preventing entry site tissue burns.

The catheter has an infusion port near the distal tip of the catheter. The infusion port may include multiple openings over a short axial distance in the wall of the catheter. In addition, a balloon may be provided between the distal tip of the catheter and the infusion port, to separate the infusion port and adjacent vein tissue. By separating the infusion port from adjacent tissue, the infusate is mixed with the blood prior to contact with the endothelial surface, preventing endothelial burns. The balloon is controlled through a lumen inside the catheter.

An external computer control system monitors and controls both the body core temperature of the patient and the flow rate of the infusate. A first temperature sensing device is provided on the outside wall of the introducer sheath to measure the patient's core body temperature, and a second temperature sensing device is placed at the distal end of the catheter. The second temperature sensing device measures blood temperature distal to the mixing port, immediately after mixing. The temperature sensing devices may be thermistors or any other suitable devices.

BRIEF DESCRIPTION OF THE DRAWINGS

The above mentioned and other features of an embodiment of this invention and the manner of obtaining them will become more apparent, and will be best understood by reference to the following description, taken in conjunction with the accompanying drawings, in which.

DETAILED DESCRIPTION

Figure 1:
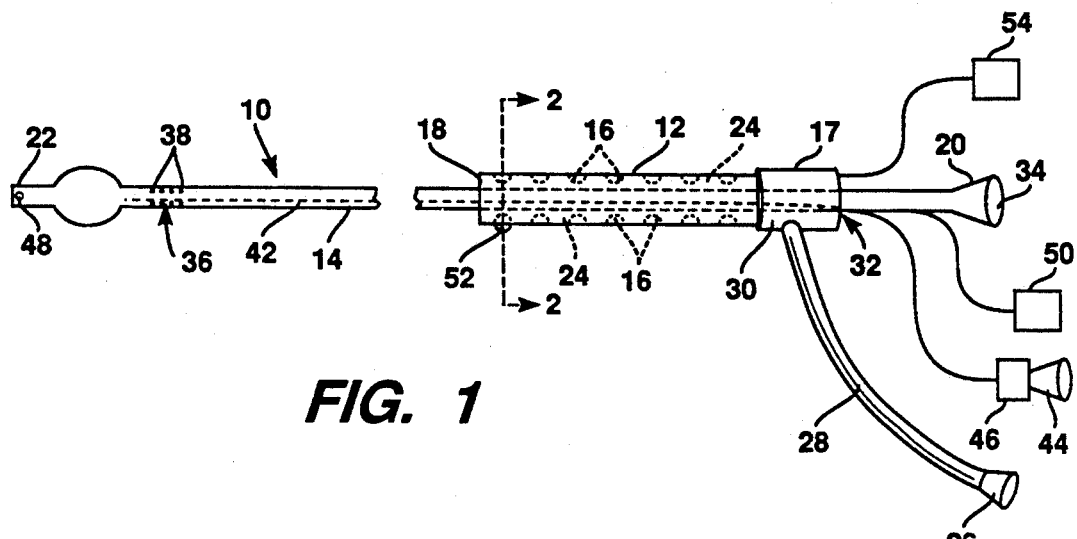
FIG. 1 is a side view of patient warming apparatus made in accordance with the principles of this invention.
Figure 2:
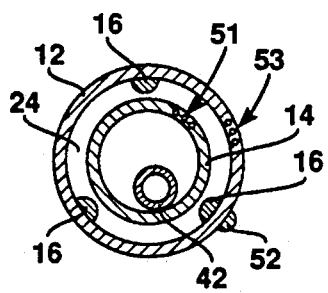
FIG. 2 is a cross-sectional view of the apparatus of FIG. 1, taken along lines 2—2 in FIG. 1.

As seen in FIGS. 1 and 2, patient warming apparatus 10 includes an introducer sheath 12 and an internal coaxial catheter 14. The catheter 14 is supported in the sheath 12 by a plurality of spaced buttons 16 so that the sheath 12 and the catheter 14 are concentric. The buttons 16 support the catheter 14 radially, but allow the catheter 14 to move axially within the sheath 12. The buttons 16 may be elongated ribs, struts or the like, but are preferably relatively small protrusions, to allow fluids to flow freely among the buttons 16 and thermally isolate the catheter 14 from the sheath 12. Also, the buttons 16 are preferably part of the sheath 12, but could also be part of the catheter 14.

Figure 5:
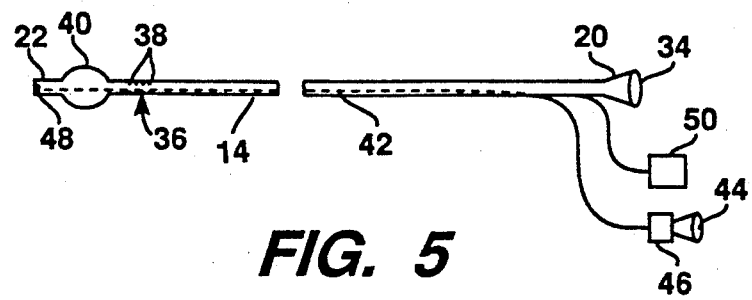
FIG. 5 is a side view of the catheter used in the apparatus of FIG. 1.

The sheath 12 has a proximal end 17 and a distal end 18 (FIG. 3), and the catheter 14 has a proximal end 20 and a distal end 22 (FIG. 5). When the catheter 14 is inserted in the sheath 12, as in FIG. 1, the catheter distal end 22 extends beyond the sheath distal end 18 (FIG. 1).

The buttons 16 center the catheter 14 in the sheath 12 and create a cooling jacket 24 between the sheath 12 and the catheter 14. Cooling fluid may be placed in the jacket 24 through a Luer lock connector 26 and a tube 28. The tube 28 is connected to a high temperature grommet and seal 30 on the proximal end 17 of the sheath 12. The seal 30 includes an opening 32 through which the catheter 14 passes.

The distal end 18 (FIG. 3) of the sheath 12 is open, so that cooling fluid in the jacket 24 may flow continuously through the sheath 12. It is contemplated that a flow rate of about 0.5–1.0 cc/min. would be adequate to thermally isolate the catheter 14 from the sheath 12, without disturbing the patient's system.

Figure 4:
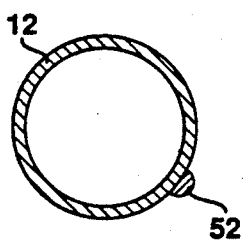
FIG. 4 is a cross-sectional view of the introducer sheath of FIG. 3, taken along lines 4—4 in FIG. 3.
Figure 3:
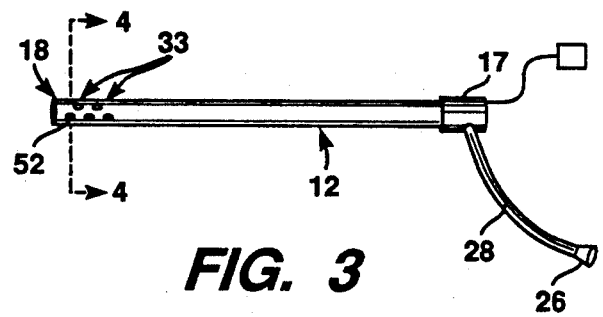
FIG. 3 is a side view of an alternate embodiment of the introducer sheath of the apparatus of FIG. 1.

An alternate embodiment of the sheath 14 is shown in FIGS. 3 and 4. The tip 18 in FIG. 3 is tapered downwardly so that the catheter 12 fits snugly in the tip 18, and is centered in the sheath 14. Exit orifices 33 are included in the sheath 14 to allow the cooling fluid to pass through the sheath 14. With this embodiment, the buttons 16 are not needed.

The catheter 14 (FIGS. 1, 2, and 5) includes a Luer lock connector 34 for injecting relatively hot fluids into the catheter 14, and an infusion port 36 near the distal end 22 of the catheter 14 for passing the heated fluids into the patient's body and mixing the heated fluids with the blood, without excessive tissue damage. The infusion port 36 may include a plurality of openings 38 which extend a short axial distance along the wall of the catheter 14.

The catheter 14 also includes a balloon 40 between the distal end 22 and the infusion port 36. The balloon 40 is controlled through a lumen 42 inside the catheter 14, and a Luer lock connector 44 and on-off valve 46 at the proximal catheter end 20. The connector 44 and valve 46 are used to inflate and deflate the balloon 40 as desired. A 1 cc balloon is contemplated.

A temperature sensing device 48 (FIG. 5) is secured to the distal catheter end 22, and an electrical connector 50 is provided at the proximal catheter end 20 for electrical connection to the sensing device 48, through wires 51 (FIG. 2). The temperature sensing device 48 measures the temperature of the patient's blood after it has been mixed with the infusate.

A second temperature sensing device 52 (FIGS. 1, 2, 3, and 4) is secured to the outside of the sheath 12, and a second connector 54 is secured to the proximal end 17 of the sheath 12. The sensing device 52 and the connector 54 are connected by wires 53 (FIG. 2). The sensing device 52 is secured near the distal sheath end 18, and may be located over a button 16 in the embodiment of FIG. 1, to better thermally isolate the sensing device 52 from the jacket 24. The sensing device 52 measures the core temperature of the patient, and its output passes through the connector 54. The sensing devices 48, 52 may be thermistors or any other suitable devices.

Figure 6:
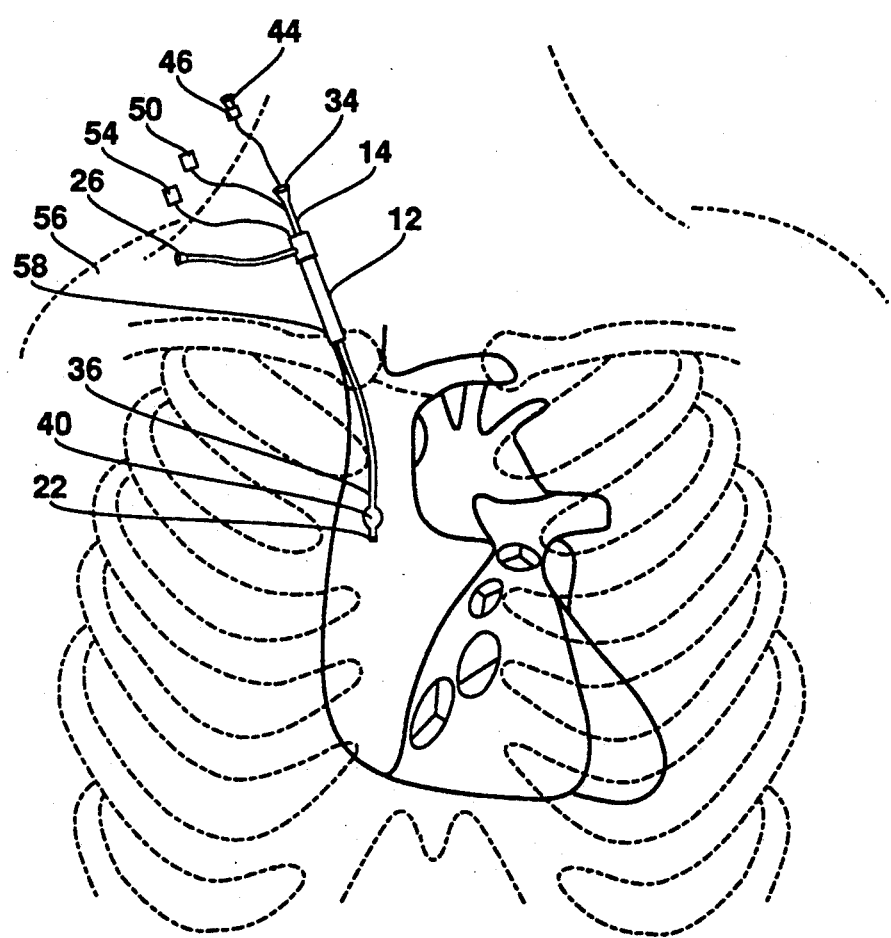
FIG. 6 is an illustration of the apparatus of FIG. 1 in use.

In use, the sheath 12 is inserted into a patient's body 56 (FIG. 6) through an artificial opening or entry site 58, using known insertion devices and techniques. After the sheath 12 is in place, the catheter 14 is placed inside the sheath through the seal 30, until the distal catheter tip 22 is in a desired part of the patient's body. The balloon 40 is then inflated to a desired size.

Cooling fluid is placed in the jacket 24 through the connector 26, and heated infusate is then infused into the body through the connector 34 of the catheter 14. The infusate may be any suitable temperature, such as about 50°–100° C.

The jacket 24 thermally isolates the patient's body from the heated fluids in the catheter 14. The balloon 40 separates the infusion port 36 from the adjacent vein tissue. By separating the infusion port from adjacent tissue in this manner, the infusate is mixed with the blood prior to contact with the endothelial surface, preventing endothelial burns.

Figure 7:
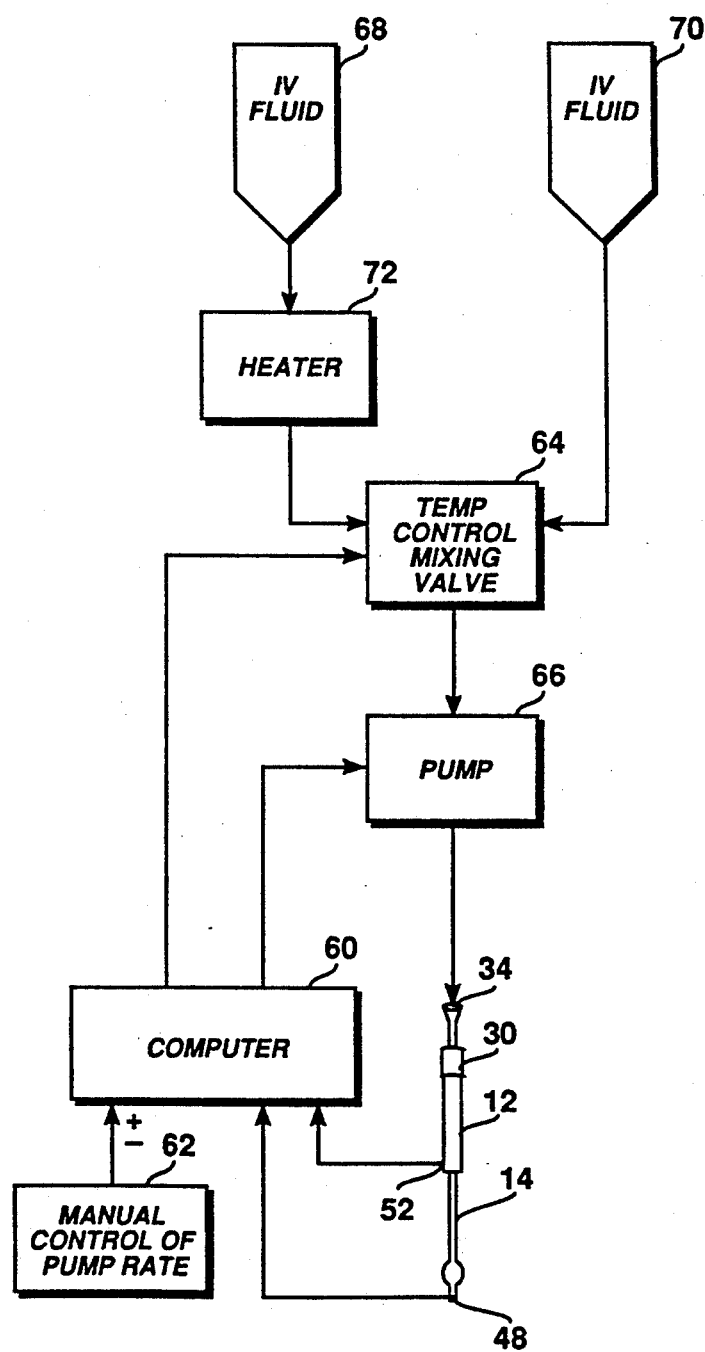
FIG. 7 is a block diagram of a control system used with the apparatus of FIG. 1.

The temperature and rate of flow of the infusate may be controlled by the control system shown in FIG. 7. The control system includes a computer 60, a manual pump rate control 62, a temperature control mixing valve 64 and a pump 66. Intravenous fluid is provided through IV sources 68, 70. The intravenous fluid in the source 68 is heated in a heater 72, and the fluids in both sources are mixed in the valve 64. The proportionate mix is determined by the computer 60 and adjusted in response to changes in the core temperature of the patient and the temperature of the patient's blood just after mixing with the infusate. As the IV solutions 68, 70 are mixed to the desired temperature in the valve 64, the resulting infusate is pumped through the pump 66, which injects the infusate into the catheter connector 34. The pump flow rate is also controlled by the computer 60, as set by the manual pump control 62.

The computer 60 monitors both the core temperature of the patient, through the temperature sensing device 52, and the temperature of the blood after mixing with the infusate, through the temperature sensing device 48. The computer 60 is programmed in a known manner so that the core temperature 48 of the patient is monitored and does not exceed predetermined levels. The temperature of the mixed blood is also monitored to prevent injury to the patient.

The computer 60 is programmed so that if the patient's core temperature is greater than 37° C., for example, the system infuses fluid which is 37° C., and if the core temperature is less than 37° C., the system heats the fluid such that the temperature of the patient's blood after mixing (measured by the sensing device 48) is about 41° C.

Figure 8:
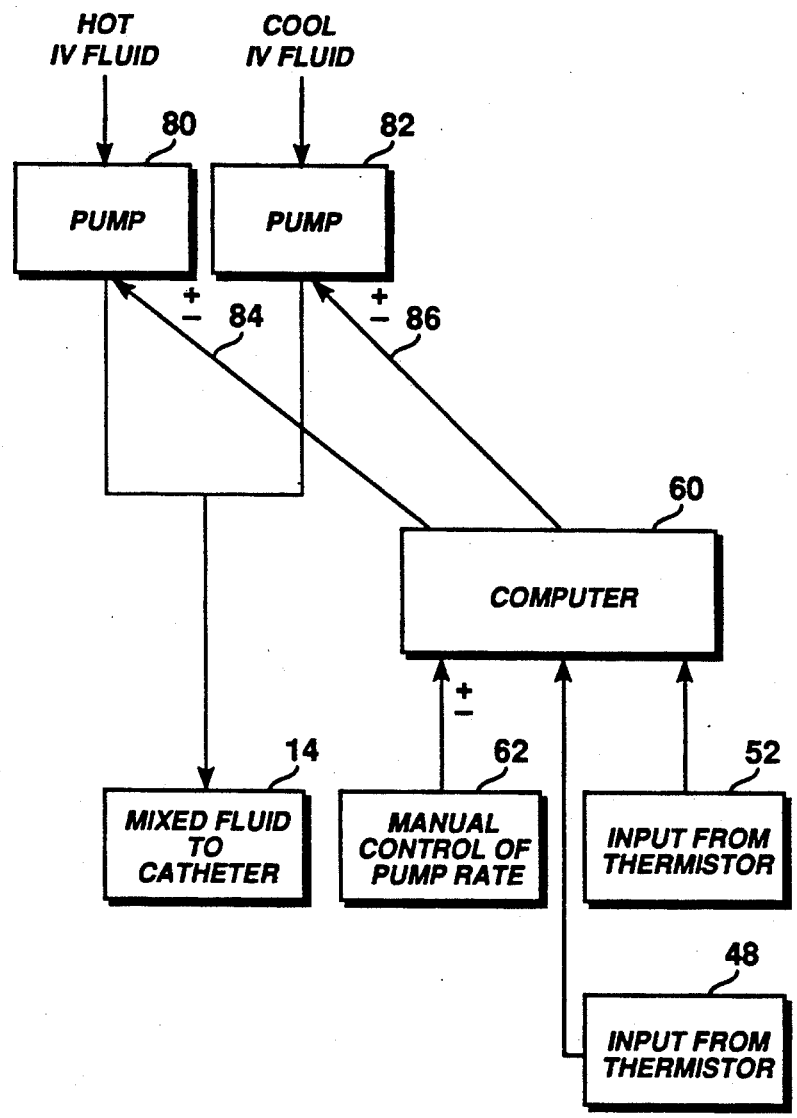
FIG. 8 is a block diagram of an alternate embodiment of the control system of FIG. 7.

Alternate embodiments of the control system are contemplated. For example, the control system of FIG. 8 includes two peristaltic pumps 80, 82, each connected to an IV source, with one containing heated fluid. The computer controls the pumps separately through wires 84, 86, to obtain the desired infusate temperature and flow rate to the catheter 14.

While the principles of the invention have been described above in connection with specific apparatus and applications, it is to be understood that this description is made only by way of example and not as a limitation on the scope of the invention.

What is claimed is:

1. Apparatus for warming a patient with heated fluids at a controlled temperature and flow rate, the patient having blood which circulates within endothelial lined vessels, the patient's blood having a core temperature inside the patient and a vessel temperature inside a selected endothelial lined vessel, comprising:

catheter means for injecting the heated fluids into the selected vessel of the patient through an opening in the patient, said catheter means including a catheter having a proximal catheter end and a distal catheter end which is to be passed through the patient opening and into the selected vessel of the patient;

means for mixing the heated fluids with the blood without excessive endothelial damage, said mixing means including a plurality of orifices near said distal catheter end for passing the heated fluids into the patient, said distal catheter end further having means for separating said fluid passing means from the patient so that substantially all of the heated fluids mix with the blood within the patient before the heated fluids reach the patient's endothelial lined vessels;

means for thermally isolating the patient opening from said catheter means, said thermal isolating means including a sheath which surrounds said catheter means at the patient opening, a cooling jacket between said sheath and said catheter means, and means between said sheath and said catheter means for spacing said sheath from said catheter; and means for controlling the temperature and the flow rate of the fluids into the patient.

2. The apparatus of claim 1 wherein said separating means comprises a balloon between said distal catheter end and said orifices.

3. The apparatus of claim 1 wherein said spacing means comprises a plurality of spaced buttons between said sheath and said catheter means.

4. The apparatus of claim 3 wherein said buttons are secured to said sheath.

5. Apparatus for warming a patient with heated fluids at a controlled temperature and flow rate, the patient having blood which circulates within endothelial lined vessels, the patient's blood having a core temperature inside the patient and a vessel temperature inside a selected endothelial lined vessel, comprising:

catheter means for injecting the heated fluids into the selected vessel of the patient through an opening in the patient, said catheter means including a catheter having a proximal catheter end and a distal catheter end which is to be passed through the patient opening and into the selected vessel of the patient;

means for mixing the heated fluids with the blood without excessive endothelial damage, said mixing means including a plurality of orifices near said distal catheter end for passing the heated fluids into the patient, said distal catheter end further having means for separating said fluid passing means from the patient so that substantially all of the heated fluids mix with the blood within the patient before the heated fluids reach the patient's endothelial lined vessels;

means for thermally isolating the patient opening from said catheter means; and means for controlling the temperature and the flow rate of the fluids into the patient, said temperature and flow rate control means having first temperature sensing means for sensing the core temperature of the patient, said control means being responsive to the temperature sensed by said first temperature sensing means.

6. The apparatus of claim 5 wherein said temperature and flow rate control means further comprises second temperature sensing means secured to said distal catheter end for sensing the vessel temperature of the patient after the heated fluids are injected into the patient and mixed with the blood of the patient, said control means being responsive to the temperatures sensed by said first and second temperature sensing means.

7. Apparatus for warming a patient with heated fluids at a controlled temperature and flow rate, the patient having blood which circulates in endothelial lined vessels, the patient's blood having a core temperature inside the patient and a vessel temperature inside a selected endothelial lined vessel, comprising:

catheter means for injecting the heated fluids into the selected vessel of the patient through an opening in the patient;

means for thermally isolating the patient opening from said catheter means, said thermal isolating means having a sheath which surrounds said catheter means at the patient opening to form a cooling jacket between said sheath and said catheter means, and spacing means between said sheath and said catheter means, said spacing means including a plurality of spaced buttons; and means for mixing the heated fluids with the blood without excessive endothelial damage.

8. The apparatus of claim 7 wherein said buttons are secured to said sheath.

9. Apparatus for arming a patient with heated fluids at a controlled temperature and flow rate, the patient having blood which circulates in endothelial lined vessels, the patient's blood having a core temperature inside the patient and a vessel temperature inside a selected endothelial lined vessel, comprising:

catheter means for injecting the heated fluids into the selected vessel of the patient through an opening in the patient;

means for thermally isolating the patient opening from said catheter means, said thermal isolating means having a sheath which surrounds said catheter means at the patient opening to form a cooling jacket between said sheath and said catheter means, and spacing means between said sheath and said catheter means;

means for mixing the heated fluids with the blood without excessive endothelial damage; and means for controlling the temperature and flow rate of the fluids into the patient, said temperature and flow rate control means having first temperature sensing means for sensing the core temperature of the patient, said control means being responsive to the temperatures sensed by said first temperature sensing means.

10. The apparatus of claim 9 wherein said temperature and flow rate control means further comprises second temperature sensing means secured to said distal catheter end for sensing the vessel temperature of the patient after the heated fluids are injected into the patient and mixed with the blood of the patient, said control means being responsive to the temperatures sensed by said first and second temperature sensing means.

* * * * *